United States Patent
Niu et al.

(10) Patent No.: US 11,001,688 B2
(45) Date of Patent: May 11, 2021

(54) ANTIMICROBIAL SILICONE RUBBER, PREPARATION METHOD THEREFOR AND USE THEREOF

(71) Applicant: Suzhou DOBIOM Medical Technology Co., Ltd., Suzhou (CN)

(72) Inventors: Zhimeng Niu, Suzhou (CN); Shanyong Zhang, Suzhou (CN)

(73) Assignee: Suzhou DOBION Medical Technology Co., Ltd., Suzhou (CN)

( * ) Notice: Subject to any disclaimer, the term of this patent is extended or adjusted under 35 U.S.C. 154(b) by 8 days.

(21) Appl. No.: 16/497,321

(22) PCT Filed: Mar. 30, 2018

(86) PCT No.: PCT/CN2018/081292
§ 371 (c)(1),
(2) Date: Sep. 24, 2019

(87) PCT Pub. No.: WO2018/219035
PCT Pub. Date: Dec. 6, 2018

(65) Prior Publication Data
US 2020/0017651 A1  Jan. 16, 2020

(30) Foreign Application Priority Data
May 31, 2017 (CN) .......................... 201710398252.8

(51) Int. Cl.
| C08J 7/12 | (2006.01) |
| A61L 29/06 | (2006.01) |
| A61L 29/16 | (2006.01) |
| A61L 31/06 | (2006.01) |
| A61L 31/16 | (2006.01) |

(52) U.S. Cl.
CPC ................ *C08J 7/12* (2013.01); *A61L 29/06* (2013.01); *A61L 29/16* (2013.01); *A61L 31/06* (2013.01); *A61L 31/16* (2013.01); *A61L 2300/404* (2013.01); *C08J 2383/04* (2013.01)

(58) Field of Classification Search
CPC ...... C08L 51/085; A61L 29/06; A61L 29/044; A61L 31/06; A61L 2300/404; C08J 2383/04
See application file for complete search history.

(56) References Cited

U.S. PATENT DOCUMENTS

2015/0005457 A1   1/2015   Ding et al.

FOREIGN PATENT DOCUMENTS

| CN | 101987887 A | 12/2012 |
| CN | 102028973 A | 2/2014 |
| CN | 104721875   | * 6/2015 |
| CN | 104721875 A | 3/2017 |
| CN | 107141502   | 9/2017 |
| KR | 20010044838 A | 6/2001 |

OTHER PUBLICATIONS

CN 104 721 875 machine translation (2015).*

* cited by examiner

*Primary Examiner* — Kuo Liang Peng
(74) *Attorney, Agent, or Firm* — Zhihua Han, WEN IP LLC

(57) ABSTRACT

Disclosed is an antimicrobial silicone rubber, functional macromolecules being chemically bonded to the surface of the silicone rubber and containing vinyl or ethynyl, and the functional macromolecules being chemically bonded to the surface of the silicone rubber by means of vinyl or ethynyl; the functional macromolecules comprise polyamino acid macromolecules of which the molecular structure is as shown in (I) and (II). The antimicrobial silicone rubber of the present invention has polyamino acid macromolecules chemically bonded to the surface of the silicone rubber and serves an antimicrobial function by means of the interaction of polyamino acid macromolecules with a negatively charged cell membrane in bacteria, providing a persistent antimicrobial effect and unlikely causing bacteria to develop any drug resistance; moreover, polyamino acid macromolecules bind to the surface of the silicone rubber by means of chemical bonding, preventing macromolecules from being precipitated and entering a cell, providing good biocompatibility.

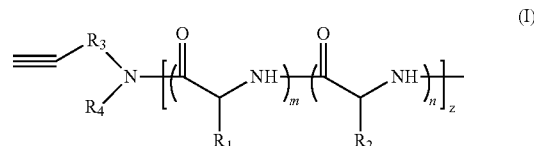

(I)

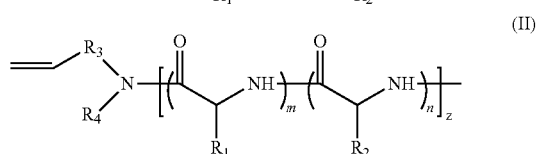

(II)

12 Claims, No Drawings

ANTIMICROBIAL SILICONE RUBBER, PREPARATION METHOD THEREFOR AND USE THEREOF

CROSS REFERENCE TO RELATED APPLICATION

This application is a national stage application of International application number PCT/CN2018/081292, filed Mar. 30, 2018, titled "ANTIMICROBIAL SILICONE RUBBER, PREPARATION METHOD THEREFOR AND USE THEREOF", which claims the priority benefit of Chinese Patent Application No. CN201710398252.8, filed on May 31, 2017, which is hereby incorporated by reference in its entirety.

TECHNICAL FIELD

The invention relates to silicon rubber, a preparation method therefor and use thereof, in particular to antimicrobial silicon rubber, a preparation method therefor and use thereof.

BACKGROUND ART

Silicone rubber has excellent bio-safety and mechanical properties. It has been widely used in medical, health care, cosmetics and other fields for its products such as urethral catheters, drainage tubes, respiratory catheters, cervical occlusion devices, and wound dressings. However, silicone rubber needs to be in contact with human tissues such as the urethra and skin for a long time during use. As an exogenous artificial material, the surface of the silicone rubber is prone to bacterial adhesion and proliferation, and even forming a biofilm, and as the silicone rubber retention time increases, the probability of bacterial infection increases. The biofilm, as a "protective umbrella" for microorganisms, can resist the effects of antibiotics on microorganisms, and even enter human blood to cause sepsis and even endanger the lives of patients. Statistically, the bacterial infection caused by the use of silicone rubber accounts for 40% of the total number of infections in the hospital each year, and is increasing year by year. Hence, the antimicrobial property of silicone rubber surface is of great importance. The development of antimicrobial silicone rubber and its products is of great significance for improving the retention period of silicone rubber, increasing the comfort of use, reducing the workload of medical care, and ensuring the safety of patients.

At present, there are two main ways to research and develop antimicrobial silicone rubber:

1) incorporating an antibiotic or an organic antimicrobial agent with silicone rubber by means of bulk addition or surface coating to inhibit the proliferation of bacteria by a specific antimicrobial group of the antibiotic. For example: in the Chinese patent CN201558397U "silicone rubber loaded with slow-release amikacin", polylactic acid-polyglycolic acid loaded with amikacin is coated on the surface of the silicone rubber to obtain the antimicrobial effect by the slow-release of amikacin. However, a large amount of antibiotics needs to be added to ensure an antimicrobial effect since the silicone rubber may indwell for a long period of time, which would cause bacteria to develop drug resistance, resulting in antibiotic failure. In the Chinese patent application CN201431691Y "An antimicrobial hydrophilic coating silicone rubber", chitin or chitosan derivatives were coated on the surface of silicone rubber to prepare antimicrobial silicone rubber. However, the chitin or chitosan derivative has a poor antimicrobial effect and has no covalent bonding with the surface of silicon rubber, causing a weak bonding force and easily fell off; and 2) compounding an inorganic silver, copper or zinc-loaded antimicrobial agent with the silicone rubber, and realizing antimicrobial effect by means of the action of the released antimicrobial metal ions ($Ag^+$, $Cu^{2+}$ or $Zn^{2+}$) or nanoparticles thereof to bacteria on the surface of the silicone rubber. For example: in the Chinese patent application CN2778285Y, "antimicrobial silicone rubber", antimicrobial silicone rubber is prepared by coating nano silver on the surface of silicone rubber; And in the Chinese patent application CN101912638A "Nano silver-loaded silica urinary catheter and production method thereof", nano silver-loaded silica is mixed into silica gel, and subjected to vulcanization and other processes to prepare an antimicrobial silicone rubber urinary catheter. However, the continuous precipitation and accumulation of antimicrobial metal ions or nanoparticles would destroy the microenvironment balance of surrounding tissues, interfere with the normal growth of surrounding cells, promote the content of intracellular reactive oxygen species (ROS) to increase, produce cytotoxicity, and lead to poor biocompatibility of silicone rubber.

It can be seen, the problem of cytotoxicity caused by bacterial resistance or separation of antimicrobial active substances cannot be avoided in the prior art.

SUMMARY OF THE INVENTION

The first technical problem to be solved by the present invention is to provide an antimicrobial silicone rubber. The antimicrobial silicone rubber of the present invention provides a persistent antimicrobial effect and unlikely causes bacteria to develop any drug resistance; antibacterial active substances do not precipitate and enter cells to cause cytotoxicity problems, providing good biocompatibility with cells.

The second technical problem to be solved by the invention is to provide a preparation method of the antimicrobial silicone rubber.

The third technical problem to be solved by the present invention is to provide a use of the antimicrobial silicone rubber.

In order to solve the first technical problem, the invention adopts the following technical solution: an antimicrobial silicone rubber, functional macromolecules being chemically bonded to the surface of the silicone rubber and containing vinyl or ethynyl, and the functional macromolecules being chemically bonded to the surface of the silicone rubber by means of vinyl or ethynyl; the functional macromolecules comprises a polyamino acid macromolecules, the molecular structure of which is shown as follows:

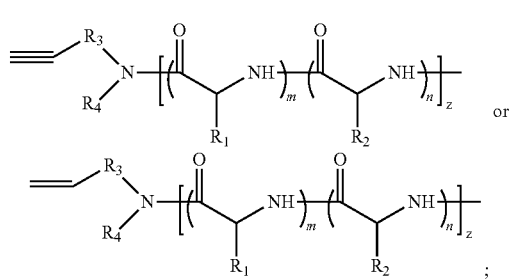

wherein $R_1$ is any one of the structures shown below:

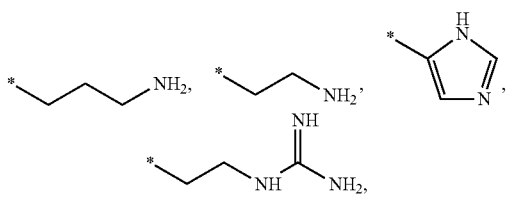

wherein $R_2$ is any one of the structures shown below:

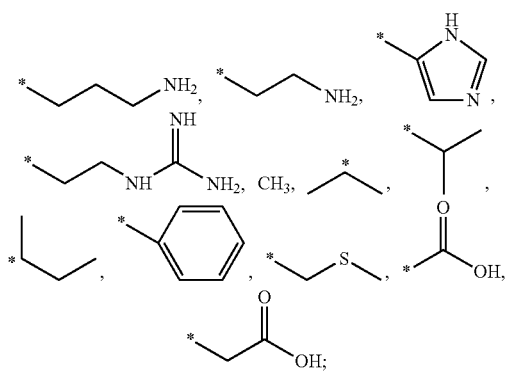

wherein $R_3$ is any one of the structures shown below:

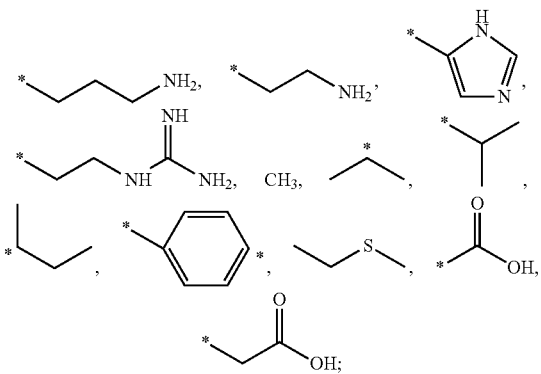

wherein $R_4$ is any one of the structures shown below:

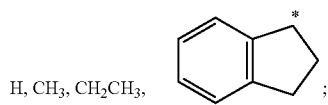

wherein m, n, z and a are all integers, m=5-10000, n=0-5000, z=1-200 and a=0-2000; "*" is a chemical bonding point of $R_1$, $R_2$, $R_3$, $R_4$ and their adjacent groups.

The polyamino acid macromolecules can be purchased directly from the market, and can also be synthesized according to well-known methods by those skilled in the art.

In the present application, preferably, the polyamino acid macromolecule is a polyamino acid homopolymer or a polyamino acid block copolymer obtained by ring-opening polymerization of an amino acid-N-carboxylic anhydride initiated by a primary or secondary amine molecule containing a vinyl or an alkynyl, and the specific preparation method is as follows:

S1, dissolving an initiator and an amino acid-N-carboxylic anhydride A in N, N-dimethylformamide or tetrahydrofuran, wherein the mass ratio of the initiator to the amino acid-N-carboxylic anhydride A is 1:10-1:1000, the mass ratio of the amino acid-N-carboxylic anhydride A to the N, N-dimethylformamide or tetrahydrofuran is 1:5-1:100; introducing nitrogen for protection; stirring for the reaction at 10-40° C. for 12-96 hours; then adding amino acid-N-carboxylic anhydride B, wherein the mass ratio of the amino acid-N-carboxylic anhydride B to the amino acid-N-carboxylic anhydride A is 0:1-1:1, and stirring for the reaction for 12-96 hours under 10-40° C.; after the reaction is finished, concentrating the solution under reduced pressure to remove the solvent, precipitating the concentrated solution in diethyl ether, and drying to obtain polyamino acid or polyamino acid with a protecting group;

The initiator has the following structural formula:

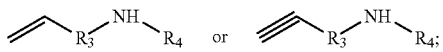

wherein $R_3$ is any one of the structures shown below:

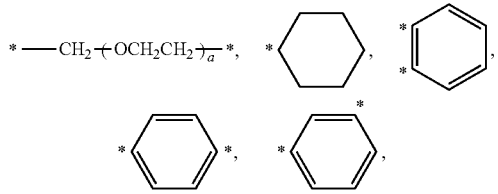

wherein $R_4$ is any one of the structures shown below:

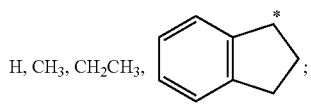

Wherein, a is an integer from 0 to 2000 and "*" is a chemical bonding point of $R_3$, $R_4$ and there adjacent groups;

S2, dissolving the polyamino acid with the protecting group by trifluoroacetic acid, adding a 33% hydrogen bromide/glacial acetic acid mixed solution under nitrogen protection and protection from light conditions, reacting for 1-3 hours at 20-40° C., depositing the product by diethyl ether, filtering, washing and drying to obtain the polyamino acid macromolecule.

The amino acid-N-carboxylic anhydride A is selected from one or more of N (ε)-benzyloxycarbonyl-L-lysine-N-carboxylic anhydride, N'-benzyloxycarbonyl-L-ornithine, L-histidine-N-carboxylic anhydride, L-arginine-N-carboxylic anhydride;

the amino acid-N-carboxylic anhydride B is selected from one or more of N (ε)-benzyloxycarbonyl-L-lysine-N-carboxylic anhydride, N'-benzyloxycarbonyl-L-ornithine-N-carboxylic anhydride, L-histidine-N-carboxylic anhydride, L-arginine-N-carboxylic anhydride, L-alanine-N-carboxylic anhydride, L-leucine-N-carboxylic anhydride, L-isoleucine-N-carboxylic anhydride, L-valine-N-carboxylic anhydride, L-phenylalanine-N-carboxylic anhydride, L-methionine-N- carboxylic anhydride, γ-benzyl-L-glutamic acid-carboxylic anhydride, β-benzyl-L-aspartic acid-carboxylic anhydride.

Preferably, the functional macromolecule may further comprise a hydrophilic molecule selected from one of N-vinylpyrrolidone and derivatives thereof, acrylic acid and derivatives thereof, vinylphosphoric acid,

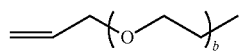

wherein b is an integer of 5-500;

Preferably, the N-vinylpyrrolidone derivatives include, but are not limited to, 5-vinyl-2-pyrrolidone; the acrylic acid derivatives include, but are not limited to, acrylamide, hydroxyethyl acrylate, hydroxypropyl acrylate, hydroxybutyl acrylate, hydroxyethyl methacrylate, hydroxypropyl methacrylate, or hydroxybutyl methacrylate.

In order to solve the second technical problem, the invention provides a preparation method of the antimicrobial silicone rubber, which comprises the following steps:

S01, preparing a functional reaction aqueous solution containing polyamino acid macromolecules and an initiator, wherein the mass concentration of the polyamino acid macromolecules in the reaction aqueous solution is 0.1-95%, and the mass of the initiator is 0.01-4% of the mass of the polyamino acid macromolecules;

S02, soaking silicon rubber in the functional reaction aqueous solution, and applying a certain initiating measures to react for 0.05-12 hours; and S03, taking out the silicon rubber, and carrying out conventional post-treatment to obtain the antimicrobial silicon rubber.

The invention provides alternative preparation method of the antimicrobial silicone rubber, comprising the following steps:

S11, preparing a functional reaction aqueous solution containing polyamino acid macromolecules, hydrophilic molecules and an initiator, wherein the total mass concentration of the polyamino acid macromolecules and the hydrophilic molecules in the aqueous solution is 0.1-95%, the mass ratio of the polyamino acid macromolecules to the hydrophilic molecules is 1:0-1:100, and the mass of the initiator is 0.01-4% of the total mass of the polyamino acid macromolecules and the hydrophilic molecules;

S12, soaking silicon rubber in the functional reaction solution, and applying a certain initiating measure to react for 0.05-12 hours;

S13, taking out the silicon rubber, and carrying out conventional post-treatment to obtain the antimicrobial silicon rubber.

Preferably, the conventional post-treatment comprises ultrasonic cleaning, drying, packaging and sterilization steps.

Preferably, the certain initiation measure is one of ultraviolet light irradiation-initiated grafting, γ ray irradiation-initiated grafting, microwave-initiated grafting and heating-initiated grafting. Preferably, the initiator is one or more of an azo radical initiator and a peroxide radical initiator; more preferably, the initiator includes, but is not limited to, one or more of ammonium persulfate, potassium persulfate, hydrogen peroxide, azobisisobutyramidine hydrochloride, and benzoyl peroxide.

Preferably, prior to performing steps S02 and S12, the surface of the silicone rubber is subjected to an activation treatment to construct a chemical reaction site on the surface thereof, wherein the chemical reaction site is surface chemically bonded with one or more of free radicals, unsaturated carbon-carbon bonds, and azide;

The activation treatment method for the silicone rubber surface includes, but is not limited to, one or more of the following methods:

method A: activating the silicone rubber surface by using argon, helium, carbon, nitrogen, oxygen, hydrogen or $H_2O$ plasma, and bonding carbon radicals, oxygen radicals or nitrogen radicals on the surface of the silicon rubber;

method B: soaking the silicon rubber in an oxidizing agent such as sulfuric acid, hydrogen peroxide, potassium permanganate, periodic acid, hypochlorous acid and the like or a mixed solution thereof for 0-120 minutes, ultrasonically washing, soaking in one or more mixed solutions of a vinyl silane coupling agent or methacryloxy silane coupling agent for 0.01-24 hours, and ultrasonically washing to bond unsaturated carbon-carbon bonds on the surface of the silicon rubber; and method C: soaking silicon rubber in an oxidizing agent such as sulfuric acid, hydrogen peroxide, potassium permanganate, periodic acid, hypochlorous acid and the like or a mixed solution thereof for 0-120 minutes, then soaking in chloropropyltrimethoxysilane for 0.01-24 hours after ultrasonic washing, then soaking the silicon rubber in a solution of N, N-dimethylformamide containing sodium azide, treating for 0.1-6 hours, and ultrasonically washing to bond azide groups on the surface of the silicon rubber.

The invention also provides uses of the antimicrobial silicone rubber in antimicrobial urethral catheters, antimicrobial wound dressings, antimicrobial respiratory catheters, an antimicrobial drainage tubes, antimicrobial gel, antimicrobial cervical occlusion devices or antimicrobial masks Compared with the prior art, the present invention has the following beneficial effects:

(1) the polyamino acid macromolecule is chemically bonded on the surface of the silicon rubber, and serves an antimicrobial function by means of the interaction of the polyamino acid macromolecules with a negatively charged cell membrane in bacteria, providing a persistent antimicrobial effect and unlikely causing bacteria to develop any drug resistance;

(2) the polyamino acid macromolecule is chemically bonded on the surface of the silicon rubber, preventing macromolecules from being precipitated and entering cells, producing cytotoxicity, and thus providing good biocompatibility.

DETAILED DESCRIPTION OF THE INVENTION

In order to more clearly illustrate the present invention, the present invention will be further described with reference to preferred embodiments. It should be understood by those skilled in the art that the following detailed description is illustrative and not restrictive, and is not intended to limit the scope of the invention.

Example 1

The invention discloses a preparation method of antimicrobial silicone rubber, comprising the following steps:

(1) sequentially dissolving polyamino acid macromolecules and potassium persulfate in water to prepare a functional reaction solution, wherein the mass ratio of the polyamino acid macromolecules, the potassium persulfate and water is 1:0.0001:99;

(2) soaking the silicon rubber in a functional reaction solution, heating to 120° C. by microwave, and treating for 0.05 hour; and (3) taking out the silicon rubber, ultrasonically cleaning twice with deionized water, airing, packaging and sterilizing to obtain the antimicrobial silicon rubber, wherein the antimicrobial silicon rubber can be used for an antimicrobial respiratory catheter.

The polyamino acid macromolecule has a structural formula as follows:

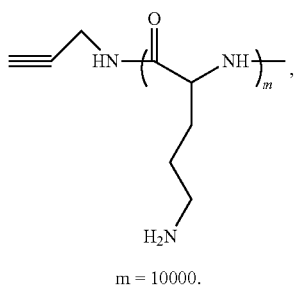

m = 10000.

The antimicrobial silicon rubber obtained in Example 1 was tested for antibacterial properties according to the standard ISO 22196:2011 "Measurement of Antibacterial Activity on Plastics And Other Non-Porous Surfaces", and the tested bacteria were *Escherichia coli* and *Staphylococcus aureus*; and the cytotoxicity test was performed based on the standard GB/T 16886.5-2003 "Medical Device Biology Evaluation" Part 5: In vitro cytotoxicity test.

According to the test, the antimicrobial silicon rubber obtained in the example 1 has the antibacterial rates of 99.92% and 99.65% against *Escherichia coli* and *Staphylococcus aureus* respectively, and the cytotoxicity is grade 0.

Example 2

The invention discloses a preparation method of antimicrobial silicone rubber, comprising the following steps:

(1) sequentially dissolving polyamino acid macromolecules, hydroxyethyl acrylate and ammonium persulfate in water to prepare a functional reaction solution, wherein the mass ratio of polyamino acid macromolecules, hydroxyethyl acrylate, ammonium persulfate and water is 1:94:3.8:5;

(2) soaking silica gel silicone rubber in the functional reaction solution, heating to 80° C. by microwave, and treating for 0.5 hour; and (3) taking out the silicon rubber, ultrasonically cleaning twice with deionized water, airing, packaging and sterilizing to obtain the antimicrobial silicon rubber, wherein the antimicrobial silicon rubber can be used for the antimicrobial ultra-slippery urethral catheter.

The polyamino acid macromolecule has a structural formula as follows:

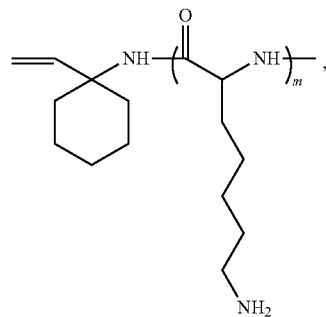

m = 5000.

The antibacterial property of the antibacterial silicone rubber obtained in Example 2 was tested according to the standard ISO 22196:2011 "Measurement of Antibacterial Activity on Plastics And Other Non-Porous Surfaces", and the tested bacteria were *Staphylococcus aureus, Pseudomonas aeruginosa* and *Candida albicans*; the cytotoxicity test was performed based on the standard GB/T 16886.5-2003 "Medical Device Biology Evaluation" Part 5: In vitro cytotoxicity test, the tested cells were L929 mouse fibroblasts.

According to the test, the antimicrobial silicon rubber obtained in the example 2 has the antibacterial rates of 99.21%, 99.78% and 98.86% respectively against *Staphylococcus aureus, Pseudomonas aeruginosa* and *Candida albicans*, and the cytotoxicity is grade 0.

Example 3

The invention discloses a preparation method of antimicrobial silicone rubber, comprising the following steps:

(1) sequentially dissolving polyamino acid macromolecules, acrylamide and azodiisobutyramidine hydrochloride in water to prepare a functional reaction solution, wherein the mass ratio of polyamino acid macromolecules, acrylamide, azodiisobutyramidine hydrochloride to water is 0.5:50:0.05:49.5;

(2) treating the surface of the silica gel silicone rubber by using oxygen plasma injection, immediately soaking the silicone rubber in a functional reaction solution after the treatment is finished, and carrying out ultraviolet irradiation treatment for 0.2 hour; and (3) taking out the silicon rubber, ultrasonically cleaning twice with deionized water, airing, packaging and sterilizing to obtain the antimicrobial silicon rubber, wherein the antimicrobial silicon rubber can be used for an antimicrobial drainage tube.

The polyamino acid macromolecule has a structural formula as follows:

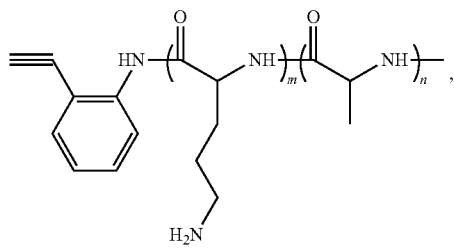

m = 5, n = 5000.

The antibacterial property of the antibacterial silicone rubber obtained in Example 3 was tested according to the standard ISO 22196:2011 "Measurement of Antibacterial Activity on Plastics And Other Non-Porous Surfaces", and the tested bacteria were *Staphylococcus epidermidis, Escherichia coli* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 3 has the antibacterial rates of 96.81%, 95.94% and 98.89% respectively against *Staphylococcus epidermidis, Escherichia coli* and *Pseudomonas aeruginosa*, and the cytotoxicity is grade 0.

Example 4

The invention discloses a preparation method of antimicrobial silicone rubber, which comprises the following steps:
(1) sequentially dissolving polyamino acid macromolecules, hydroxypropyl acrylate and benzoyl peroxide in water to prepare a functional reaction solution, wherein the mass ratio of polyamino acid macromolecules, hydroxypropyl acrylate, benzoyl peroxide and water is 1:1:0.04:98;
(2) treating the surface of the silicon rubber by using oxygen plasma injection, immediately soaking the silicon rubber in the functional reaction solution after the treatment is finished, and irradiating γ rays for 12 hours; and
(3) taking out the silicone rubber, ultrasonically cleaning twice with deionized water, airing, packaging and sterilizing to obtain the antimicrobial silicone rubber, wherein the antimicrobial silicone rubber can be used for antimicrobial silicone rubber gel.

The polyamino acid macromolecule has a structural formula as follows:

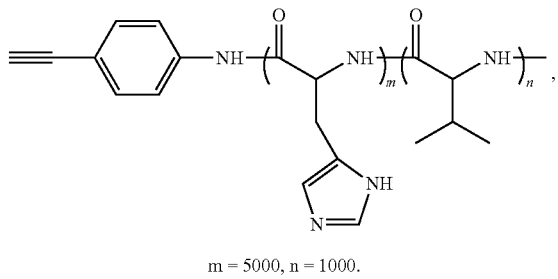

$m = 5000, n = 1000.$

The antibacterial property of the antibacterial silicone rubber obtained in Example 4 was tested according to the standard ISO 22196:2011 "Measurement of Antibacterial Activity on Plastics And Other Non-Porous Surfaces", and the tested bacteria were *Staphylococcus aureus, Escherichia coli* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 4 has antibacterial rates of 99.81%, 99.94% and 99.89% respectively against *Staphylococcus aureus, Escherichia coli* and *Pseudomonas aeruginosa*, and the cytotoxicity is grade 0.

Example 5

The invention discloses a preparation method of antimicrobial silicone rubber, comprising the following steps:

(1) sequentially dissolving polyamino acid macromolecule, hydroxybutyl acrylate and benzoyl peroxide in water to prepare a functional reaction solution, wherein the mass ratio of polyamino acid macromolecule, hydroxybutyl acrylate, benzoyl peroxide and water is 1:5:0.02:94;
(2) treating the surface of the silica gel silicone rubber by using a mixed solution of sulfuric acid and hydrogen peroxide for 1 minute, ultrasonically washing, soaking the silica gel silicone rubber in vinyltriethoxysilane for 0.01 hour, ultrasonically washing to bond unsaturated carbon-carbon bonds on the surface of the silicone rubber;
(3) soaking the silicon rubber treated in the step (2) in the functional reaction solution, heating to 60° C., and reacting for 1 hour; and
(4) taking out the silicone rubber, ultrasonically cleaning twice with deionized water, airing, packaging and sterilizing to obtain the antimicrobial silicone rubber, wherein the antimicrobial silicone rubber can be used for the antimicrobial silicone rubber wound dressings.

The polyamino acid macromolecule has a structural formula as follows:

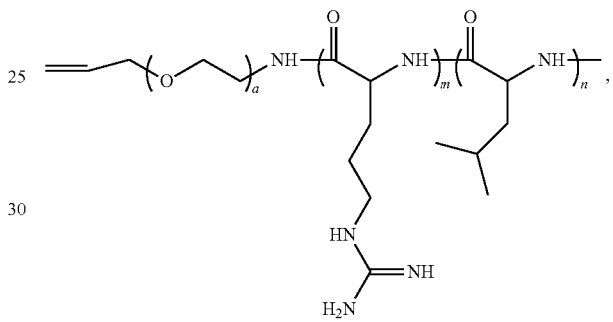

$m = 1000, n = 1000,$ and $a = 2000.$

The antibacterial property of the antibacterial silicone rubber obtained in Example 5 was tested according to the standard ISO 22196:2011 "Measurement of Antibacterial Activity on Plastics And Other Non-Porous Surfaces", and the tested bacteria were *Staphylococcus aureus, Escherichia coli* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 5 has antibacterial rates of 99.21%, 99.97% and 99.16% respectively against *Staphylococcus aureus, Escherichia coli* and *Pseudomonas aeruginosa*, and the cytotoxicity is grade 0.

Example 6

The invention discloses a preparation method of antimicrobial silicone rubber, comprising the following steps:

(1) sequentially dissolving polyamino acid macromolecules, hydroxypropyl methacrylate and hydrogen peroxide in water to prepare a functional reaction solution, wherein the mass ratio of polyamino acid macromolecules, hydroxypropyl methacrylate, hydrogen peroxide and water is 1:20: 0.1:79;
(2) soaking silica gel silicone rubber in γ-methacryloyloxytriethoxysilane for 24 hours, and ultrasonically washing to bond unsaturated carbon-carbon bonds on the surface of the silicone rubber; and (3) soaking the silicon rubber treated in the step (2) in the functional reaction solution, heating to 80° C., and reacting for 1 hour; and (4) taking out the silicon rubber, ultrasonically cleaning twice with deionized water, airing, packaging and sterilizing to obtain the antimicrobial silicon rubber, wherein the antimicrobial silicon rubber can be used for antimicrobial hydrophilic silicon rubber masks.

The polyamino acid macromolecule has a structural formula as follows:

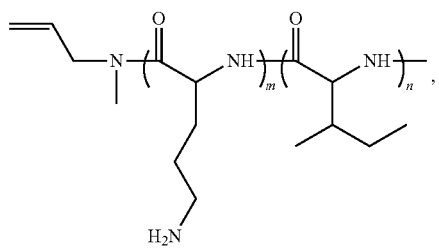

m = 2000, and n = 1000.

The antibacterial property of the antibacterial silicone rubber obtained in Example 6 was tested according to the standard ISO 22196:2011 "Measurement of Antibacterial Activity on Plastics And Other Non-Porous Surfaces", and the tested bacteria were *Staphylococcus aureus* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicon rubber obtained in the example 6 has antibacterial rates of 99.88% and 99.75% respectively against *Staphylococcus aureus* and *Pseudomonas aeruginosa*, and the cytotoxicity is grade 0.

Example 7

The invention discloses a preparation method of antimicrobial silicone rubber, comprising the following steps:

(1) sequentially dissolving polyamino acid macromolecules, hydroxybutyl methacrylate and benzoyl peroxide in water to prepare a functional reaction solution, wherein the mass ratio of polyamino acid macromolecules, hydroxybutyl methacrylate, benzoyl peroxide and water is 2:30:0.2:68;

(2) soaking silica gel silicone rubber in chloropropyltrimethoxysilane for 2 hours, then soaking the silicone rubber into a solution of N, N-dimethylformamide containing sodium azide for 0.1 hour, and ultrasonically washing to bond azide groups on the surface of the silicone rubber;

(3) soaking the silicon rubber treated in the step (2) in the functional reaction solution, and performing ultraviolet radiation treatment for 1 hour; and (4) taking out the silicon rubber, ultrasonically cleaning twice with deionized water, airing, packaging and sterilizing to obtain the antimicrobial silicon rubber, wherein the antimicrobial silicon rubber can be used for an antimicrobial silicon rubber cervical occlusion device.

The polyamino acid macromolecule has a structural formula as follows:

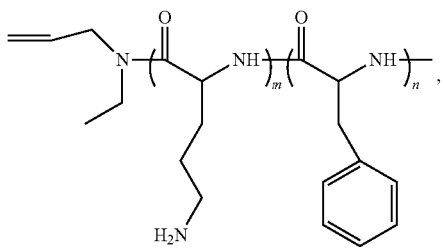

m = 5000, and n = 100.

The antibacterial property of the antibacterial silicone rubber obtained in Example 7 was tested according to the standard ISO 22196:2011 "Measurement of Antibacterial Activity on Plastics And Other Non-Porous Surfaces", and the tested bacteria were *Staphylococcus epidermidis* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicon rubber obtained in the example 7 has antibacterial rates of 99.28% and 99.58% respectively against *Staphylococcus epidermidis* and *Pseudomonas aeruginosa*, and the cytotoxicity is grade 0.

Example 8

The invention discloses a preparation method of antimicrobial silicone rubber, comprising the following steps:

(1) sequentially dissolving polyamino acid macromolecules, hydroxyethyl methacrylate and azodiisobutymmidine hydrochloride in water to prepare a functional reaction solution, wherein the mass ratio of polyamino acid macromolecules, hydroxyethyl methacrylate, azodiisobutymmidine hydrochloride to water is 10:10:0.25:80;

(2) treating the surface of the silicone rubber by nitrogen plasma injection, immediately soaking the silicone rubber in the functional reaction solution after the treatment is finished, and performing ultraviolet irradiation treatment for 2 hours; and (3) taking out the silicone rubber, ultrasonically cleaning twice with deionized water, airing, packaging and sterilizing to obtain the antimicrobial silicone rubber, wherein the antimicrobial silicone rubber can be used for the antimicrobial silicone rubber urethral catheter.

The polyamino acid macromolecule has a structural formula as follows:

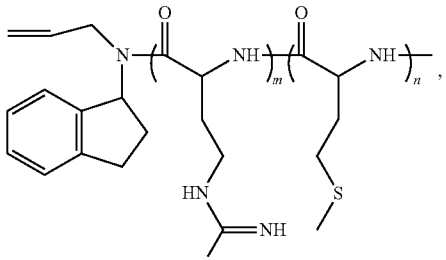

m = 4000, and n = 1000.

The antibacterial property of the antibacterial silicone rubber obtained in Example 8 was tested according to the standard ISO 22196:2011 "Measurement of Antibacterial Activity on Plastics And Other Non-Porous Surfaces", and the tested bacteria were *Staphylococcus epidermidis* and *Candida albicans*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 8 has antibacterial rates of 99.28% and 99.58% respectively against *Staphylococcus epidermidis* and *Candida albicans*, and the cytotoxicity is grade 0.

Example 9

The invention discloses a preparation method of antimicrobial silicone rubber, comprising the following steps:

(1) sequentially dissolving polyamino acid macromolecules, 5-vinyl-2-pyrrolidone and azodiisobutyramidine hydrochloride in water to prepare a functional reaction solution, wherein the mass ratio of polyamino acid macromolecules, 5-vinyl-2-pyrrolidone, azodiisobutyramidine hydrochloride to water is 8:12:0.2:80;

(2) treating the surface of the silica gel silicone rubber by using argon plasma injection, immediately soaking the silicone rubber in the functional reaction solution after the treatment is finished, and performing ultraviolet irradiation treatment for 4 hours; and (3) taking out the silicon rubber, ultrasonically cleaning twice with deionized water, airing, packaging and sterilizing to obtain antimicrobial silicon rubber, wherein the antimicrobial silicon rubber can be used for an antimicrobial silicon rubber respiratory catheter.

The polyamino acid macromolecule has a structural formula as follows:

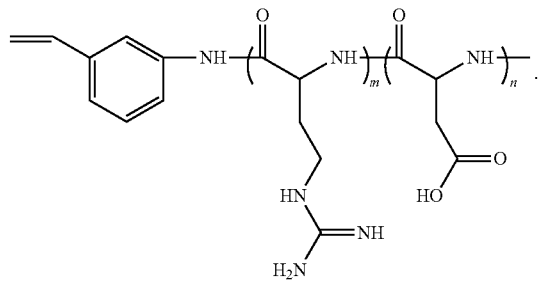

m = 8000, and n = 500.

The antibacterial property of the antibacterial silicone rubber obtained in Example 9 was tested according to the standard ISO 22196:2011 "Measurement of Antibacterial Activity on Plastics And Other Non-Porous Surfaces", and the tested bacteria were *Staphylococcus aureus* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 9 has antibacterial rates of 99.74% and 99.92% respectively against *Staphylococcus aureus* and *Pseudomonas aeruginosa*, and the cytotoxicity is grade 0.

Example 10

The invention discloses a preparation method of antimicrobial silicone rubber, comprising the following steps:

(1) sequentially dissolving polyamino acid macromolecules, 5-vinyl-2-pyrrolidone and azodiisobutyramidine hydrochloride in water to prepare a functional reaction solution, wherein the mass ratio of polyamino acid macromolecules, 5-vinyl-2-pyrrolidone, azodiisobutyramidine hydrochloride and water is 8:40:0.2:52;

(2) treating the surface of the silica gel silicone rubber by using a potassium permanganate solution for 120 minutes, ultrasonically washing, soaking the silica gel silicone rubber in vinyltrimethoxysilane for 0.1 hour, and ultrasonically washing to bond unsaturated carbon-carbon bonds on the surface of the silicone rubber;

(3) soaking the silicon rubber treated in the step (2) in the functional reaction solution, heating to 80° C., and reacting for 1 hour; and (4) taking out the silicone rubber, ultrasonically cleaning twice with deionized water, airing, packaging and sterilizing to obtain the antimicrobial silicone rubber, wherein the antimicrobial silicone rubber can be used for the antimicrobial ultra-slippery silicone rubber urethral catheter.

The polyamino acid macromolecule has a structural formula as follows:

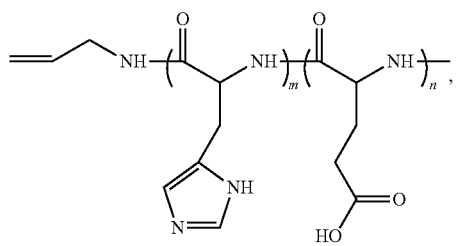

m = 2000, and n = 500.

The antibacterial property of the antibacterial silicone rubber obtained in Example 10 was tested according to the standard ISO 22196:2011 "Measurement of Antibacterial Activity on Plastics And Other Non-Porous Surfaces", and the tested bacteria were *Staphylococcus aureus*, and *Candida albicans*; the cytotoxicity test was performed based on the standard GB/T 16886.5-2003 "Medical Device Biology Evaluation" Part 5: In vitro cytotoxicity test, the tested cells were L929 mouse fibroblasts.

According to the test, the antimicrobial silicone rubber obtained in the example 10 has antibacterial rates of 99.74% and 97.92% respectively against *Staphylococcus aureus* and *Candida albicans*, and the cytotoxicity is grade 0.

Example 11

The invention discloses a preparation method of antimicrobial silicone rubber, comprising the following steps:

(1) sequentially dissolving polyamino acid macromolecules, N-vinylpyrrolidone, potassium persulfate and azodiisobutyramidine hydrochloride in water to prepare a functional reaction solution, wherein the mass ratio of polyamino acid macromolecules, N-vinylpyrrolidone, potassium persulfate and azodiisobutyramidine hydrochloride water is 8:12:0.1:0.1:80;

(2) treating the surface of the silica gel silicone rubber by using argon plasma injection, immediately soaking the silicone rubber in the functional reaction solution after the treatment is finished, and irradiating γ rays for 8 hours; and (3) taking out the silicone rubber, ultrasonically cleaning twice with deionized water, airing, packaging and sterilizing to obtain the antimicrobial silicone rubber, wherein the antimicrobial silicone rubber can be used for the antimicrobial ultra-slippery silicone rubber urethral catheter.

The polyamino acid macromolecule has a structural formula as follows:

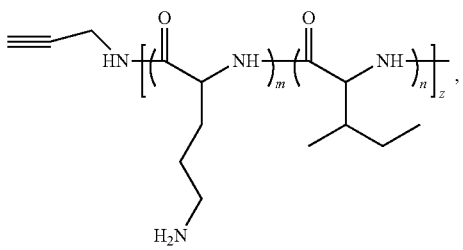

m = 500, n = 500, and z = 200.

The antibacterial property of the antibacterial silicone rubber obtained in Example 11 was tested according to the standard ISO 22196:2011 "Measurement of Antibacterial Activity on Plastics And Other Non-Porous Surfaces", and the tested bacteria were *Staphylococcus aureus*, and *Candida albicans*; the cytotoxicity test was performed based on the standard GB/T 16886.5-2003 "Medical Device Biology Evaluation" Part 5: In vitro cytotoxicity test, the tested cells were L929 mouse fibroblasts.

According to the test, the antimicrobial silicone rubber obtained in the example 11 has antibacterial rates of 99.74% and 97.92% respectively against *Staphylococcus aureus* and *Candida albicans*, and the cytotoxicity is grade 0.

Example 12

The invention discloses a preparation method of antimicrobial silicone rubber, comprising the following steps:

(1) sequentially dissolving polyamino acid macromolecules, vinyl phosphoric acid and potassium persulfate in water to prepare a functional reaction solution, wherein the mass ratio of polyamino acid macromolecules, vinyl phosphoric acid, potassium persulfate and water is 5:25:0.6:70;

(2) soaking silica gel silicone rubber in the functional reaction solution, heating to 80° C. by microwave, and treating for 0.5 hour; and (3) taking out the silicon rubber, ultrasonically cleaning twice with deionized water, airing, packaging and sterilizing to obtain the antimicrobial silicon rubber, wherein the antimicrobial silicon rubber can be used for an antimicrobial respiratory catheter.

The polyamino acid macromolecule has a structural formula as follows:

The antibacterial property of the antibacterial silicone rubber obtained in Example 12 was tested according to the standard ISO 22196:2011 "Measurement of Antibacterial Activity on Plastics And Other Non-Porous Surfaces", and the tested bacteria were *Staphylococcus aureus* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 12 has antibacterial rates of 96.74% and 92.92% respectively against *Staphylococcus aureus* and *Pseudomonas aeruginosa*, and the cytotoxicity is grade 0.

Example 13

The invention discloses a preparation method of antimicrobial silicone rubber, comprising the following steps:

(1) sequentially dissolving polyamino acid macromolecules,

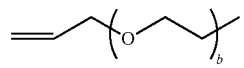

(b=5) and hydrogen peroxide in water to prepare a functional reaction solution, wherein the mass ratio of polyamino acid macromolecules,

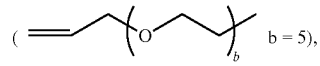

hydrogen peroxide to water is 5:35:1:60;

(2) soaking the silicon rubber in the functional reaction solution, heating to 80° C., and treating for 3 hours; and (3) taking out the silicone rubber, ultrasonically cleaning twice with deionized water, airing, packaging and sterilizing to obtain the antimicrobial silicone rubber, wherein the antimicrobial silicone rubber can be used for the antimicrobial silicone rubber wound dressings.

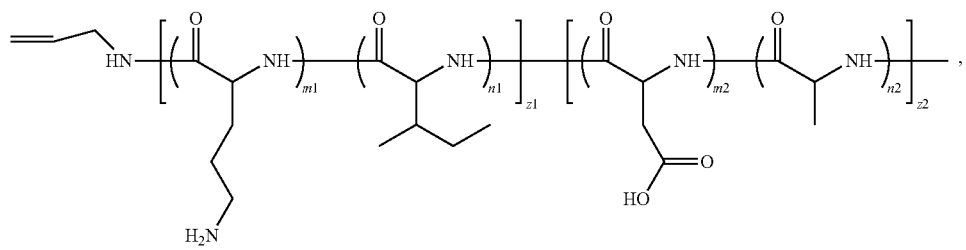

m1 = 1000, n1 = 500, z1 = 5, m2 = 200, n2 = 200, and z2 = 10.

The polyamino acid macromolecule has a structural formula as follows:

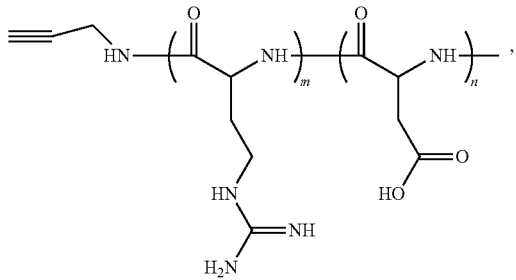

m = 1000, and n = 500.

The antibacterial property of the antibacterial silicone rubber obtained in Example 13 was tested according to the standard ISO 22196:2011 "Measurement of Antibacterial Activity on Plastics And Other Non-Porous Surfaces", and the tested bacteria were *Staphylococcus aureus, Escherichia coli* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 13 has antibacterial rates of 99.84%, 99.92% and 97.65% respectively against *Staphylococcus aureus, Escherichia coli* and *Pseudomonas aeruginosa*, and the cytotoxicity is grade 0.

Example 14

The invention discloses an antimicrobial silicone rubber and method thereof, comprising the following steps:

(1) sequentially dissolving polyamino acid macromolecule,

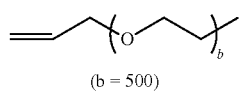

(b = 500)

and potassium persulfate in water to prepare a functional reaction solution, wherein the mass ratio of polyamino acid macromolecule,

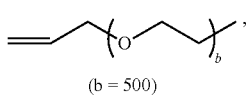

(b = 500)

potassium persulfate to water is 10:40:1:50;

(2) soaking silica gel silicone rubber in the functional reaction solution, heating to 120° C. by microwave, and treating for 5 hour; and (3) taking out the silicone rubber, ultrasonically cleaning twice with deionized water, airing, packaging and sterilizing to obtain the antimicrobial silicone rubber, wherein the antimicrobial silicone rubber can be used for the antimicrobial ultra-slippery silicone rubber urethral catheter.

The polyamino acid macromolecule has a structural formula as follows:

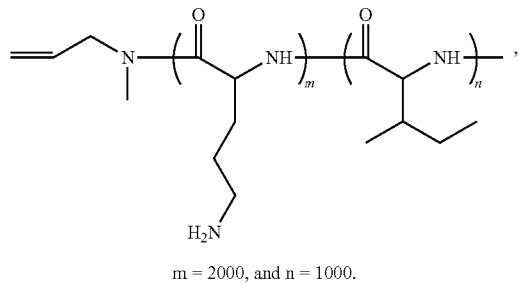

m = 2000, and n = 1000.

The antibacterial property of the antibacterial silicone rubber obtained in Example 14 was tested according to the standard ISO 22196:2011 "Measurement of Antibacterial Activity on Plastics And Other Non-Porous Surfaces", and the tested bacteria were *Staphylococcus aureus, Escherichia coli* and *Pseudomonas aeruginosa*; the cytotoxicity test was performed based on the standard GB/T 16886.5-2003 "Medical Device Biology Evaluation" Part 5: In vitro cytotoxicity test, and the tested cells were L929 mouse fibroblasts.

According to the test, the antimicrobial silicone rubber obtained in the example 14 has antibacterial rates of 99.44%, 99.88% and 96.65% respectively against *Staphylococcus aureus, Escherichia coli* and *Pseudomonas aeruginosa*, and the cytotoxicity is grade 0.

It should be understood that the above-described embodiments of the present invention are merely illustrative of the present invention, and are not intended to limit the embodiments of the present invention. Other variations and modifications will occur to those skilled in the art in light of the above teachings. It is not intended to be exhaustive of all embodiments and all such obvious variations and modifications as fall within the scope of the invention will come within the scope of the appended claims.

The invention claimed is:

1. An antimicrobial silicone rubber, wherein functional macromolecule is chemically bonded to the surface of the silicone rubber and the functional macromolecule contain vinyl or ethynyl, and the functional macromolecule is chemically bonded to the surface of the silicone rubber by means of vinyl or ethynyl; the functional macromolecule comprises polyamino acid macromolecule, the molecular structure of which is shown as follows:

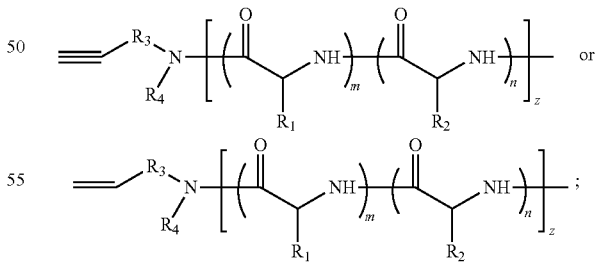

wherein $R_1$ is any one of the structures shown below:

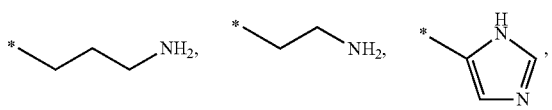

-continued

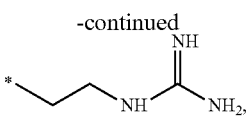

wherein R₂ is any one of the structures shown below:

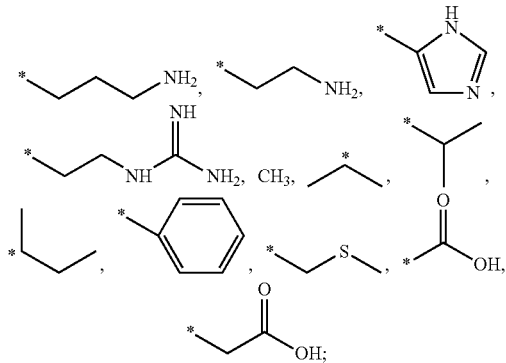

wherein R₃ is any one of the structures shown below:

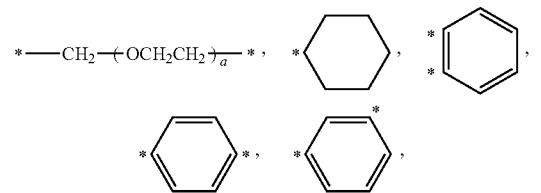

and
wherein R₄ is any one of the structures shown below:

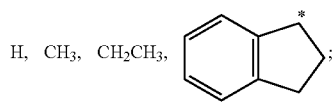

wherein m, n, z and a are all integers, and m=5-10000, n=0-5000, z=1-200 and a=0-2000; "*" is a chemical binding point of R₁, R₂, R₃, R₄ and their adjacent groups.

2. The antimicrobial silicone rubber of claim 1, wherein the polyamino acid macromolecule is a polyamino acid homopolymer or a polyamino acid block copolymer obtained by ring-opening polymerization of an amino acid-N-carboxylic anhydride initiated by a primary or secondary amine molecule containing a vinyl or an alkynyl, the method of preparation comprising:

S1, dissolving an initiator and an amino acid-N-carboxylic anhydride A in N, N-dimethylformamide or tetrahydrofuran, wherein the mass ratio of the initiator to the amino acid-N-carboxylic anhydride A is 1:10-1:1000, the mass ratio of the amino acid-N-carboxylic anhydride to the N, N-dimethylformamide or tetrahydrofuran is 1:5-1:100, and introducing nitrogen for protection; stirring for the reaction at 10-40° C. for 12-96 hours;

then adding amino acid N-carboxylic anhydride B, wherein the mass ratio of the amino acid N-carboxylic anhydride B to the amino acid N-carboxylic anhydride A is 0:1-1:1, and stirring for the reaction at 10-40° C. for 12-96 hours; after the reaction is finished, concentrating the solution under reduced pressure to remove the solvent, precipitating the concentrated solution in diethyl ether, and drying to obtain polyamino acid or polyamino acid with a protecting group;

the initiator has a following structural formula:

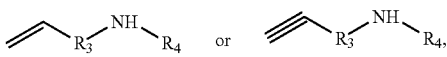

wherein R₃ is any one of the structures shown below:

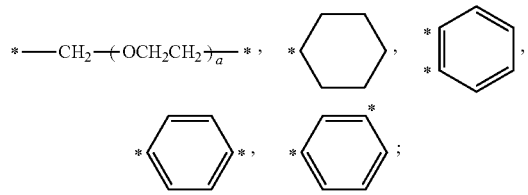

wherein R₄ is any one of the structures shown below:

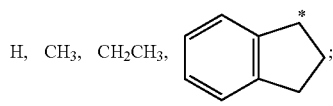

wherein a is an integer from 0 to 2000 and "*" is a chemical bonding point of R₃, R₄ and there adjacent groups;

S2, for the polyamino acid with the protecting group, further dissolving the polyamino acid with the protecting group by trifluoroacetic acid, adding a 33% hydrogen bromide in a mixture consisting of the hydrogen bromide and glacial acetic acid under nitrogen protection and protection from light conditions, reacting for 1-3 hours at 20-40° C., settling the product by diethyl ether, filtering, washing and drying to obtain the polyamino acid macromolecule.

3. The antimicrobial silicone rubber of claim 2, wherein:
the amino acid-N-carboxylic anhydride A is selected from one or more of N (ε)-benzyloxycarbonyl-L-lysine-N-carboxylic anhydride, N'-benzyloxycarbonyl-L-ornithine, L-histidine-N-carboxylic anhydride, and L-arginine-N-carboxylic anhydride;
the amino acid-N-carboxylic anhydride B is selected from one or more of N (ε)-benzyloxycarbonyl-L-lysine-N-carboxylic anhydride, N'-benzyloxycarbonyl-L-ornithine-N-carboxylic anhydride, L-histidine-N-carboxylic anhydride, L-arginine-N-carboxylic anhydride, L-alanine-N-carboxylic anhydride, L-leucine-N-carboxylic anhydride, L-isoleucine-N-carboxylic anhydride, L-valine-N-carboxylic anhydride, L-phenylalanine-N-carboxylic anhydride, L-methionine-N-carboxylic anhydride, γ-benzyl-L-glutamic acid-carboxylic anhydride, and β-benzyl-L-aspartic acid-carboxylic anhydride.

4. The antimicrobial silicone rubber of claim 1, wherein:
the functional macromolecule further comprises a hydrophilic molecule selected from N-vinylpyrrolidone and its derivatives, acrylic acid and its derivatives, vinyl phosphate, and

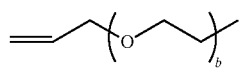

wherein b is an integer of 5-500.

5. The antimicrobial silicone rubber of claim 4, wherein:
the N-vinylpyrrolidone derivatives 5-vinyl-2-pyrrolidone;
the acrylic acid derivatives include acrylamide, hydroxyethyl acrylate, hydroxypropyl acrylate, hydroxybutyl acrylate, hydroxyethyl methacrylate, hydroxypropyl methacrylate and hydroxybutyl methacrylate.

6. A method of preparation for antimicrobial silicone rubber of claim 1, wherein, comprising the following steps:
S01, preparing a functional reaction aqueous solution containing polyamino acid macromolecules and an initiator, wherein the mass concentration of the polyamino acid macromolecules in the reaction aqueous solution is 0.1-95%, and the mass of the initiator is 0.01-4% of the mass of the polyamino acid macromolecules;
S02, soaking silicon rubber in the functional reaction aqueous solution, and applying a certain initiating measures to react for 0.05-12 hours; and
S03, taking out the silicon rubber, and carrying out post-treatment to obtain the antimicrobial silicon rubber.

7. The method of claim 6, wherein:
the post-treatment includes ultrasonic cleaning, drying, packaging, and sterilization steps;
the certain initiation measure adopts ultraviolet light irradiation-initiated grafting, γ-ray radiation-initiated grafting, microwave-initiated grafting, and heating-initiated grafting;
the initiator is one or more of an azo radical initiator and a peroxide radical initiator.

8. The method of claim 6, wherein:
prior to performing step S02, the surface of the silicone rubber is subjected to activation treatment;
the method of activation treatment for the silicone rubber surface includes, one or more of the following methods:
method A: activating the silicone rubber surface by using argon, helium, carbon, nitrogen, oxygen, hydrogen or $H_2O$ plasma, and bonding carbon radicals, oxygen radicals or nitrogen radicals on the surface of the silicon rubber;
method B: soaking the silicon rubber in an oxidizing agent selected from the group of sulfuric acid, hydrogen peroxide, potassium permanganate, periodic acid, hypochlorous acid, or a mixed solution thereof for 0-120 minutes, ultrasonically washing, soaking in one or more mixed solutions of a vinyl silane coupling agent or methacryloxy silane coupling agent for 0.01-24 hours, and ultrasonically washing to bond unsaturated carbon-carbon bonds on the surface of the silicon rubber;
method C: soaking silicon rubber in an oxidizing agent selected from the group of sulfuric acid, hydrogen peroxide, potassium permanganate, periodic acid, hypochlorous acid, or a mixed solution thereof for 0-120 minutes, ultrasonically washing, soaking in chloropropyltrimethoxysilane for 0.01-24 hours, then soaking the silicon rubber in a solution of N, N-dimethylformamide containing sodium azide, treating for 0.1-6 hours, and ultrasonically washing to bond azide groups on the surface of the silicon rubber.

9. The method of preparation for antimicrobial silicone rubber of claim 1, wherein, comprising the following steps:
S11, preparing a functional reaction aqueous solution containing polyamino acid macromolecules, hydrophilic molecules and an initiator, wherein the total mass concentration of the polyamino acid macromolecules and the hydrophilic molecules in the aqueous solution is 0.1-95%, the mass ratio of the polyamino acid macromolecules to the hydrophilic molecules is 1:0-1:100, and the mass of the initiator is 0.01-4% of the total mass of the polyamino acid macromolecules and the hydrophilic molecules;
S12, soaking silicon rubber in the functional reaction solution, and applying a certain initiating measure to react for 0.05-12 hours; and
S13, taking out the silicon rubber, and carrying out post-treatment to obtain the antimicrobial silicon rubber.

10. The method of claim 9, wherein:
the post-treatment includes ultrasonic cleaning, drying, packaging, and sterilization steps;
the certain initiation measure adopts ultraviolet light irradiation-initiated grafting, γ-ray radiation-initiated grafting, microwave-initiated grafting, and heating-initiated grafting;
the initiator is one or more of an azo radical initiator and a peroxide radical initiator.

11. The method of claim 9, wherein:
prior to performing step S12, the surface of the silicone rubber is subjected to activation treatment;
the method of activation treatment for the silicone rubber surface includes, one or more of the following methods:
method A: activating the silicone rubber surface by using argon, helium, carbon, nitrogen, oxygen, hydrogen or $H_2O$ plasma, and bonding carbon radicals, oxygen radicals or nitrogen radicals on the surface of the silicon rubber;
method B: soaking the silicon rubber in an oxidizing agent selected from the group of sulfuric acid, hydrogen peroxide, potassium permanganate, periodic acid, hypochlorous acid, or a mixed solution thereof for 0-120 minutes, ultrasonically washing, soaking in one or more mixed solutions of a vinyl silane coupling agent or methacryloxy silane coupling agent for 0.01-24 hours, and ultrasonically washing to bond unsaturated carbon-carbon bonds on the surface of the silicon rubber;
method C: soaking silicon rubber in an oxidizing agent selected from the group of
sulfuric acid, hydrogen peroxide, potassium permanganate, periodic acid, hypochlorous acid, or a mixed solution thereof for 0-120 minutes, ultrasonically washing, soaking in chloropropyltrimethoxysilane for 0.01-24 hours, then soaking the silicon rubber in a solution of N, N-dimethylformamide containing sodium azide, treating for 0.1-6 hours, and ultrasonically washing to bond azide groups on the surface of the silicon rubber.

12. Use of antimicrobial silicone rubber of claim 1 in antimicrobial urethral catheters, antimicrobial wound dressings, antimicrobial respiratory catheters, antimicrobial drainage tubes, antimicrobial gel, antimicrobial cervical occlusion device or antimicrobial masks by providing the antimicrobial silicone rubber in the above devices.

* * * * *